(12) United States Patent
Zannis et al.

(10) Patent No.: US 7,857,851 B2
(45) Date of Patent: Dec. 28, 2010

(54) IMPLANT SYSTEM WITH SIZING TEMPLATES

(75) Inventors: Anthony D. Zannis, Fort Wayne, IN (US); Herbert E. Schwartz, Fort Wayne, IN (US); Danny E. McAdams, Warsaw, IN (US); Brian A. Magee, Gig Harbor, WA (US); Andrew M. Jacobs, Fort Wayne, IN (US)

(73) Assignee: Depuy Products, Inc., Warsaw, IN (US)

( * ) Notice: Subject to any disclaimer, the term of this patent is extended or adjusted under 35 U.S.C. 154(b) by 1077 days.

(21) Appl. No.: 11/261,204

(22) Filed: Oct. 28, 2005

(65) Prior Publication Data
US 2006/0095049 A1     May 4, 2006

Related U.S. Application Data

(60) Provisional application No. 60/623,366, filed on Oct. 29, 2004.

(51) Int. Cl.
A61F 2/08     (2006.01)
(52) U.S. Cl. .................... 623/14.12; 606/102; 33/511
(58) Field of Classification Search ............. 623/14.12; 606/102, 87–89; 33/511, 512, 514.2
See application file for complete search history.

(56) References Cited

U.S. PATENT DOCUMENTS

| | | |
|---|---|---|
| 4,873,976 A | 10/1989 | Schreiber |
| 4,880,429 A | 11/1989 | Stone |
| 5,007,934 A | 4/1991 | Stone |
| 5,108,438 A | 4/1992 | Stone |
| 5,242,448 A | 9/1993 | Pettine et al. |
| 5,306,311 A | 4/1994 | Stone |
| 5,320,633 A | 6/1994 | Allen |
| 5,374,268 A | 12/1994 | Sander |
| 5,569,252 A | 10/1996 | Justin |
| 5,681,353 A | 10/1997 | Li |
| 5,702,462 A | 12/1997 | Oberlander |
| 5,735,903 A | 4/1998 | Li |
| 5,980,524 A | 11/1999 | Justin |
| 5,993,475 A | 11/1999 | Lin |

(Continued)

FOREIGN PATENT DOCUMENTS

EP     1 442 726 A1     8/2004

(Continued)

OTHER PUBLICATIONS

U.S. Appl. No. 60/483,804, Jacobs et al.

(Continued)

*Primary Examiner*—Corrine M McDermott
*Assistant Examiner*—Rebecca Straszheim

(57) ABSTRACT

Surgical instruments for use in sizing tissue defects and selecting an appropriate implant for the defect include sizing templates. The sizing templates are sized and shaped to correspond to the size and shape of the implants. The sizing templates may be retractable into a tube for use in arthroscopic surgery. The retractable sizing templates are resilient to allow them to be retracted into a small diameter tube, and to expand on release from the tube to the desired size and shape. The method of using the instrument set is also described.

25 Claims, 9 Drawing Sheets

U.S. PATENT DOCUMENTS

| | | |
|---|---|---|
| 6,019,739 A | 2/2000 | Rhee |
| 6,042,610 A | 3/2000 | Li |
| 6,056,778 A | 5/2000 | Grafton |
| 6,152,935 A | 11/2000 | Kammerer |
| 6,156,044 A | 12/2000 | Kammerer |
| 6,293,961 B2 | 9/2001 | Schwartz |
| 6,306,156 B1 | 10/2001 | Clark |
| 6,306,159 B1 | 10/2001 | Schwartz |
| 6,319,271 B1 | 11/2001 | Schwartz |
| 6,427,351 B1 | 8/2002 | Matthews |
| 6,638,312 B2 | 10/2003 | Plouhar |
| 7,160,333 B2 | 1/2007 | Plouhar |
| 7,163,563 B2 | 1/2007 | Schwartz |
| 7,201,917 B2 | 4/2007 | Malaviya |
| 7,473,259 B2 | 1/2009 | Jacobs et al. |
| 2002/0111679 A1* | 8/2002 | Zucherman et al. ...... 623/17.11 |
| 2002/0156530 A1* | 10/2002 | Lambrecht et al. ....... 623/17.16 |
| 2003/0021827 A1 | 1/2003 | Malaviya |
| 2003/0023316 A1 | 1/2003 | Brown |
| 2003/0032961 A1 | 2/2003 | Pelo |
| 2003/0033021 A1 | 2/2003 | Plouhar |
| 2003/0033022 A1 | 2/2003 | Plouhar |
| 2003/0036797 A1 | 2/2003 | Malaviya |
| 2003/0036801 A1 | 2/2003 | Schwartz |
| 2003/0044444 A1 | 3/2003 | Malaviya |
| 2003/0049299 A1 | 3/2003 | Malaviya |
| 2003/0074075 A1 | 4/2003 | Thomas |
| 2003/0078617 A1 | 4/2003 | Schwartz |
| 2004/0059431 A1 | 3/2004 | Plouhar |
| 2004/0073110 A1 | 4/2004 | Stewart et al. |
| 2004/0143344 A1 | 7/2004 | Malaviya |
| 2004/0166169 A1 | 8/2004 | Malaviya |
| 2004/0220574 A1 | 11/2004 | Pelo |
| 2004/0267276 A1 | 12/2004 | Camino et al. |
| 2004/0267277 A1 | 12/2004 | Zannis et al. |
| 2004/0267304 A1 | 12/2004 | Zannis et al. |
| 2005/0149159 A1* | 7/2005 | Andreas et al. ............ 623/1.11 |
| 2005/0203541 A1 | 9/2005 | Steffensmeier |
| 2005/0249771 A1 | 11/2005 | Malaviya |
| 2005/0249772 A1 | 11/2005 | Malaviya |
| 2006/0089621 A1 | 4/2006 | Fard |
| 2006/0095048 A1 | 5/2006 | Zannis et al. |
| 2006/0095053 A1 | 5/2006 | Zannis et al. |
| 2006/0095054 A1 | 5/2006 | Zannis et al. |
| 2006/0111726 A1 | 5/2006 | Felt |
| 2006/0211953 A1 | 9/2006 | Zannis et al. |
| 2007/0129811 A1 | 6/2007 | Plouhar |
| 2008/0065120 A1 | 3/2008 | Zannis et al. |

FOREIGN PATENT DOCUMENTS

| | | |
|---|---|---|
| JP | 2000300508 A | 10/2000 |
| WO | WO 94/16762 A | 8/1994 |

OTHER PUBLICATIONS

U.S. Appl. No. 10/172,347, Chun et al.

U.S. Appl. No. 60/623,624, Zannis et al.

European Search Report dated Feb. 13, 2006, Application No. 05256710.4.

Office Action's dated Feb. 8, 2008, Nov. 3, 2009 and Apr. 24, 2009 in related U.S. Appl. No. 11/261,041, filed Oct. 28, 2005, now abandoned.

O'Connor's Textbook of Arthroscopic Surgery, $2^{nd}$ ed., 1992, Chapter 19.

* cited by examiner

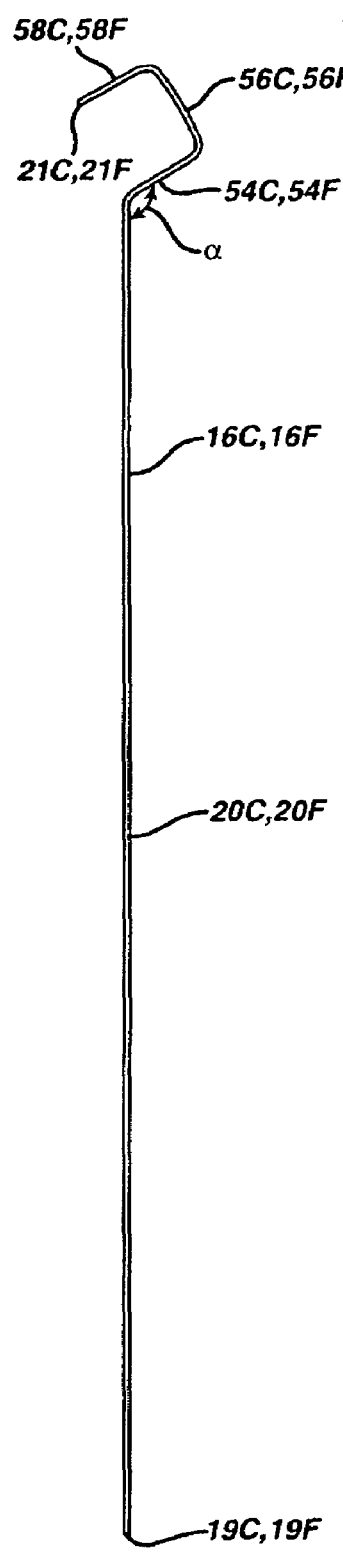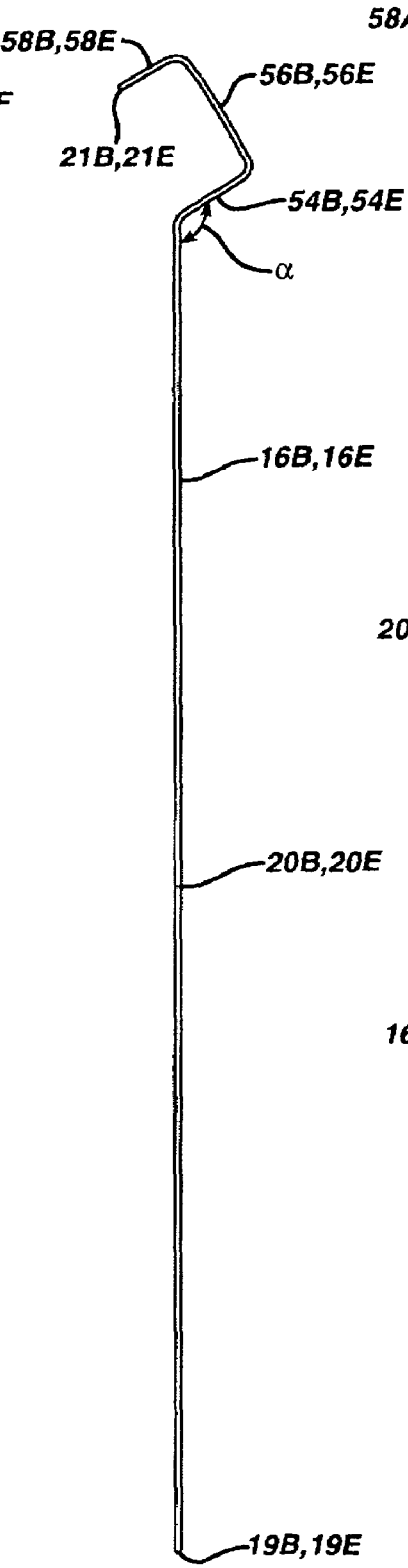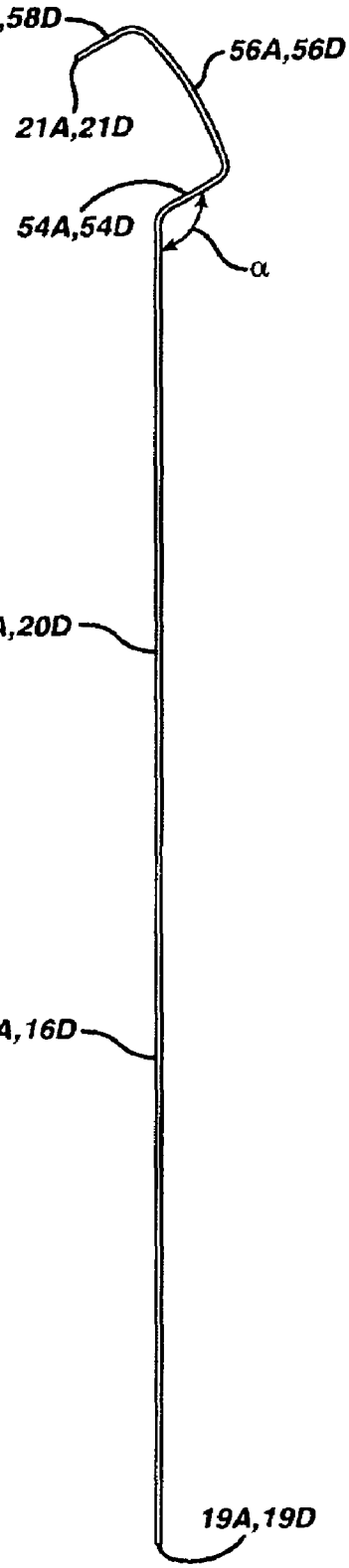

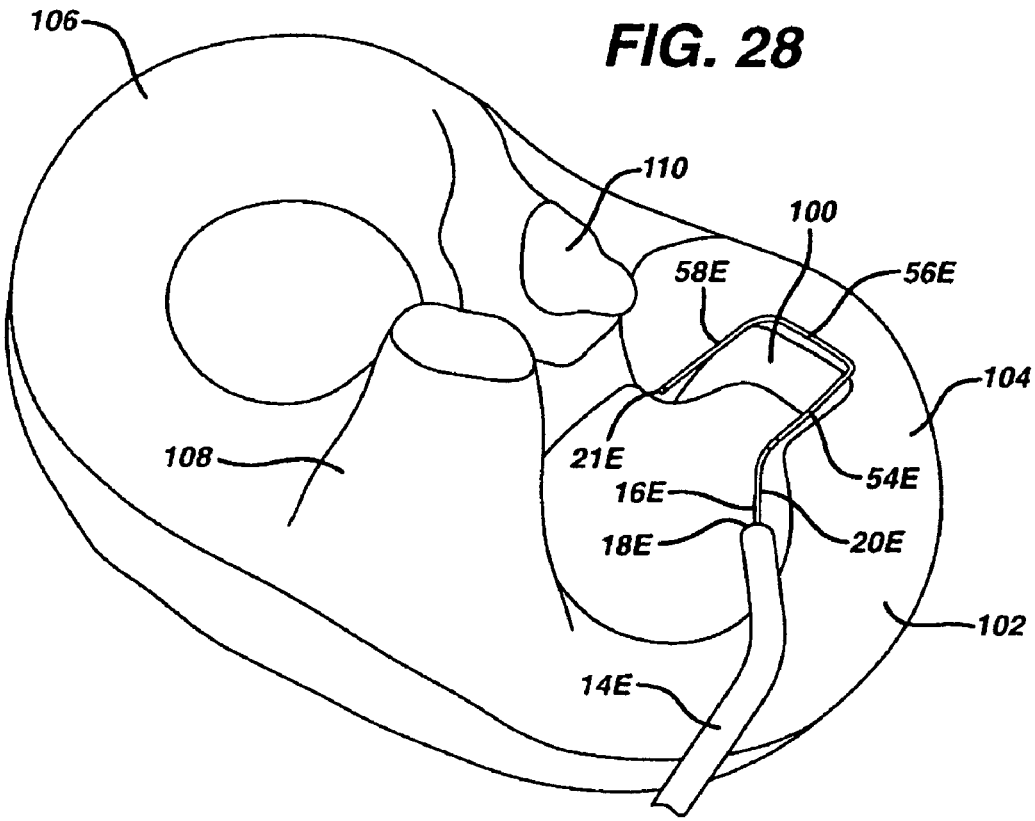
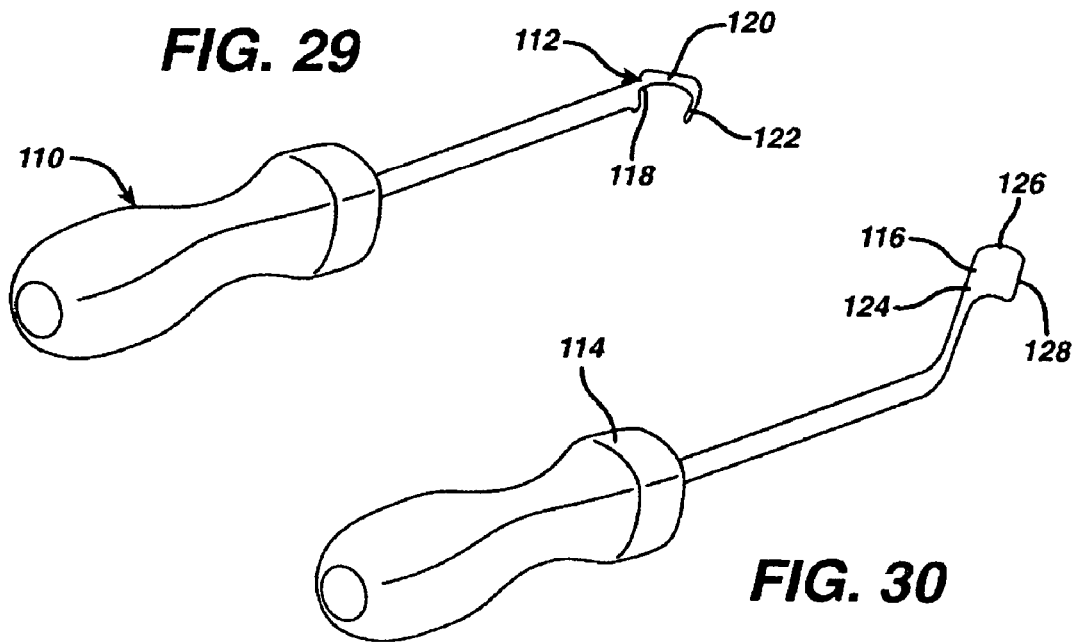

IMPLANT SYSTEM WITH SIZING TEMPLATES

This application claims the benefit of U.S. Provisional Application No. 60/623,366, filed on Oct. 29, 2004, by Anthony D. Zannis, Danny E. McAdams, Brian A. Magee, Herbert E. Schwartz and Andrew M. Jacobs entitled "Implant System and Method with Sizing Templates," which is incorporated by reference herein in its entirety.

FIELD OF THE INVENTION

The present invention relates to implants and surgical instruments and more particularly to surgical instrument sets that can be used to intraoperatively select the most appropriate implant for repair of a tissue defect.

BACKGROUND OF THE INVENTION

Various types of MIS are being performed by surgeons, including laparascopy, endoscopy and arthroscopy surgery. In arthroscopy, small incisions are made at the affected joint to form portals for the insertion of instruments, including a small lens and lighting system (an arthroscope). The arthroscope is connected to a viewing device, such as a television camera to allow the surgeon to see the interior of the joint. Other instruments are inserted through other portals to perform a variety of tasks. For example, the surgical instrument may include an implement for manipulating native tissue (for example, tissue grasping, tissue cutting, bone abrading), or an implement for introducing and implanting a therapeutic device.

Typical surgical instruments used in arthroscopic procedures include rongeurs, such as the Kerrison rongeur, punch forceps, basket forceps, suction punches and cup curet, for example. Examples of arthroscopic instruments are described and illustrated in O'Connor's Textbook of Arthroscopic Surgery, $2^{nd}$ ed., 1992, Chapter 19.

In many surgical settings, it is often necessary for the surgeon to make measurements between two points. Due to the confined spaces of arthroscopic surgery, measuring such distances is often quite difficult, particularly when the measurement needed is larger than the size of the incision or transverse to the direction of the incision. Arthroscopic knee surgery provides many such situations. For example, it may be helpful if a surgeon could measure the size of a defect in the meniscus of a knee, to aid in choosing the appropriate method to repair the defect.

An arthroscopic measuring device is disclosed in U.S. Pat. No. 6,427,351B1, which is incorporated by reference herein in its entirety. The device disclosed in that patent provides a handle and an extension. The extension has a distal tip for intraoperative insertion into the body through an incision. Two wires extend from a block in the handle through passageways in two separate tubes that comprise the extension. The block is connected to an actuator element. The actuator elements disclosed can be moved back and forth in a direction parallel to the longitudinal axis of the handle to move the wires out of an into the tubes. At their distal ends, the tubes diverge at a fixed angle so that the distance between the ends of the wires increases as the wires are pushed further outward and decreases as the wires are pulled back into the handle. Calibrations on the handle correspond with the distance between the ends of the wires so that the surgeon can determine one or more of the dimensions of a defect in the bone or cartilage.

Although the arthroscopic measuring device disclosed in U.S. Pat. No. 6,427,351B1 provides a useful surgical tool, operation of the actuating mechanism disclosed can be difficult for the surgeon, particularly due to friction as the wires are pushed through the divergent tube endings. In addition, use of that device may require that the surgeon use both hands to hold the handle and move the actuating mechanism. Finally, use of that device may not allow for repeatable measurements of the tissue and changes in the tissue over time.

Determining the size and location of a defect at a tissue site, such as the meniscus of the knee joint, can be useful in several arthroscopic procedures. Common surgical procedures for treating meniscal damage include tear repairs and menisectomies. A tear repair is most commonly performed when the tear is a clean longitudinal vertical lesion in the vascular red zone of the meniscus. The basic strategy is to stabilize the tear by limiting or eliminating radial separation of the faces of the tear when the meniscus is load bearing. Many devices and surgical procedures exist for repairing meniscal tears by approximating the faces of the meniscus at the tear. Examples of such devices and procedures are disclosed in the following U.S. Pat. Nos. 6,319,271; 6,306,159; 6,306,156; 6,293,961; 6,156,044; 6,152,935; 6,056,778; 5,993,475; 5,980,524; 5,702,462; 5,569,252; 5,374,268; 5,320,633; and 4,873,976.

Menisectomies involve the surgical removal of part of the meniscus. Such procedures have generally been performed in cases of radial tears, horizontal tears, vertical longitudinal tears outside the vascular zone, complex tears, or defibrillation. Although menisectomies provide immediate relief to the patient, in the long term the absence of part of the meniscus can cause cartilage wear on the condylar surface, eventually leading to arthritic conditions in the joint.

A variety of orthopaedic implants are available for treating damaged soft tissue. Orthopaedic implants for treatment of damaged menisci are disclosed in the following U.S. Pat. Nos. 6,042,610; 5,735,903; 5,681,353; 5,306,311; 5,108,438; 5,007,934; and 4,880,429.

The sizes and shapes of meniscal defects, including the gaps left following menisectomies, can vary from patient to patient. Typically, orthopaedic implants for treating such defects would be provided in a variety of sizes. To select the appropriate implant for a patient, the surgeon would typically use an arthroscopic probe to approximate the size of the defect. However, due to a large margin of error in such approximations, it is desirable to provide surgeons with a more accurate way to select the most appropriate implant for a particular defect.

SUMMARY OF THE INVENTION

The present invention provides an instrument set and a surgical technique for sizing a tissue defect so that the most appropriate size of implant is selected for the defect.

In one aspect, the present invention provides a surgical sizing instrument comprising a hollow tube and elongated sizing template. The hollow tube has a proximal end and a distal end. The elongated sizing template extends through the hollow tube, and includes proximal end, a distal end, an intermediate portion between the proximal end and distal end, a first resilient segment adjacent to the intermediate portion, and a second resilient segment adjacent to the first resilient segment and positioned between the first resilient segment and the distal end of the elongated sizing template. The elongated sizing template is reciprocable in the hollow tube between an extended position and a retracted position. The first resilient segment and second resilient segment are received within the hollow tube when the elongated sizing template is in the retracted position and exposed outside of the hollow tube when the elongate sizing template is in the extended position. The first resilient segment and second resilient segment have a first relative orientation when the elongated sizing template is in the extended position and a second relative orientation when the elongated sizing template is in the retracted position. The first relative orientation being different from the second relative orientation.

In another aspect, the present invention provides a surgical sizing instrument set comprising first and second surgical sizing instruments. Both surgical sizing instruments include a hollow tube and an elongated sizing template. The hollow tubes have a proximal end and a distal end. Each of the elongated sizing templates extends through one hollow tube Each elongate sizing template has a proximal end, a distal end, an intermediate portion between the proximal end and distal end, a first resilient segment adjacent to the intermediate portion, and a second resilient segment adjacent to the first resilient segment and positioned between the first resilient segment and the distal end of the elongated sizing template. The elongated sizing templates are reciprocable in the hollow tubes between extended positions and retracted positions. In each instrument, the first resilient segment and second resilient segment have a first angular relationship when the elongated sizing template is in the extended position and a second angular relationship when the elongated sizing template is in the retracted position. In each, the first angular relationship is different from the second angular relationship.

In another aspect, the present invention provides a surgical instrument having a proximal end and a distal end. The instrument comprises a handle at the proximal end and a tube extending distally from the handle. The tube defines a channel. The instrument also comprises a first gear, a second gear and an elongated member. The first gear is rotatably mounted to the handle, and has a plurality of grooved teeth. The second gear is rotatably mounted to the handle, and has a plurality of grooved teeth intermeshed with the grooved teeth of the first gear. The grooves of the intermeshed teeth of the first gear and second gear define a passageway aligned with the channel of the tube. The elongated member extends through the passageway and into the channel of the tube. The elongated member is movable in a proximal direction by rotating the first gear in one direction and movable in the distal direction by rotating the first gear in the opposite direction.

In another aspect, the present invention provides a surgical implant system. The system comprises first and second implants and first and second sizing instruments. The first implant has a width and a length and the second implant has a width and a length. At least one of the width and length of the second implant is larger than the corresponding dimension of the first implant. The first surgical sizing instrument includes a hollow tube and an elongated sizing template. The hollow tube has a proximal end and a distal end. The elongated sizing template extends through the hollow tube, and has a proximal end, a distal end, an intermediate portion between the proximal end and distal end, a first resilient segment adjacent to the intermediate portion, a second resilient segment adjacent to the first resilient segment and positioned between the first resilient segment and the distal end of the elongated sizing template. The elongated sizing template is reciprocable in the hollow tube between an extended position and a retracted position. The first resilient segment has a length corresponding with the width of the first implant and the second resilient segment has a length corresponding with the length of the first implant. The first resilient segment and second resilient segment have a first angular relationship when the elongated sizing template is in the extended position and a second angular relationship when the elongated sizing template is in the retracted position. The first angular relationship is different from the second angular relationship. The second surgical sizing instrument includes a hollow tube and an elongated sizing template. The hollow tube has a proximal end and a distal end. The an elongated sizing template extends through the hollow tube and has a proximal end, a distal end, an intermediate portion between the proximal end and distal end, a first resilient segment adjacent to the intermediate portion, a second resilient segment adjacent to the first resilient segment and positioned between the first resilient segment and the distal end of the elongated sizing template. The elongated sizing template of the second sizing instrument is reciprocable in the hollow tube between an extended position and a retracted position. The first resilient segment of the elongated sizing template of the second sizing instrument has a length corresponding with the width of the second implant and the second resilient segment has a length corresponding with the length of the second implant. The first resilient segment and second resilient segment of the second sizing instrument have a first angular relationship when the elongated sizing template is in the extended position and a second angular relationship when the elongated sizing template is in the retracted position, the first angular relationship being different from the second angular relationship.

In another aspect, the present invention provides a method of repairing soft tissue. Soft tissue is removed to create a defect having a first side having a length and orientation and a second non-parallel side having a length and orientation. First and second implants are provided. The first implant includes a first side having a length and orientation and a second non-parallel side having a length and orientation. The second implant also has a first side having a length and orientation and a second non-parallel side having a length and orientation. First and second sizing templates are provided. The first sizing template includes a first side having a length and orientation corresponding to the length and orientation of the first side of the first implant and a second side having a length and orientation corresponding to the length and orientation of the second side of the first implant. The second sizing template includes a first side having a length and orientation corresponding to the length and orientation of the first side of the second implant and a second side having a length and orientation corresponding to the length and orientation of the second side of the second implant. One of the sizing templates is introduced to the area of the defect and positioned with its first side at the first side of the defect and with its second side at the second side of the defect. The surgeon can then determine whether the introduced sizing template fits the defect. The sizing template is removed and one of the implants is introduced to the area of the defect and positioned in the defect.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 16 is a plan view of the small sizing template of the instrument set of FIGS. 1-2;

FIG. 17 is a plan view of the medium sizing template of the instrument set of FIGS. 1-2;

FIG. 18 is a plan view of the large sizing template of the instrument set of FIGS. 1-2;

FIG. 28 is a diagrammatic perspective view of a meniscus, illustrating use of one of the instruments of the present invention to size a defect in the meniscus;

FIG. 29 is a perspective view of an alternative embodiment of an instrument useful in sizing a defect; and FIG. 30 is a perspective view of another alternative embodiment of an instrument useful in sizing a defect.

DETAILED DESCRIPTION

Figure 1:
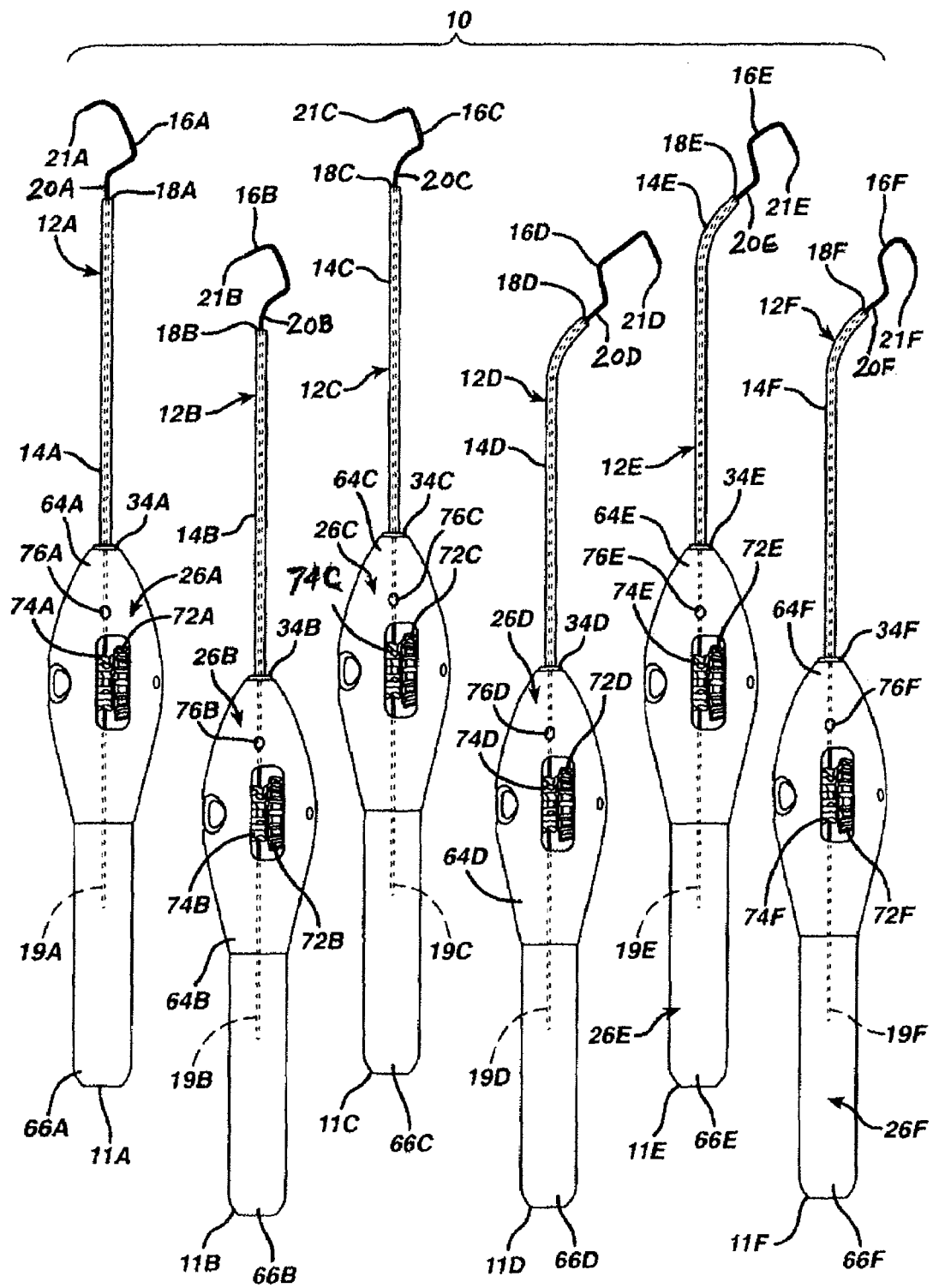
FIG. 1 is a top plan view of a set of surgical instruments with sizing templates in an extended position.

Surgical instruments embodying the principles of the present invention are illustrated in the accompanying drawings. FIG. 1 illustrates a surgical instrument set 10 comprising a plurality of individual instruments 12A, 12B, 12C, 12D, 12E, 12F that can be used to determine the appropriate size of implant to be used in treating a tissue defect, such as a meniscal defect. As used herein, "defect" is intended to include both tissue tears and gaps in tissue left after part of the tissue has been removed, such as through a meniscectomy. Although the illustrated instrument set 10 includes six individual instruments, it should be understood that the principles of the present invention are applicable to instrument sets having fewer or more than six instruments, as well as to individual instruments; the present invention should not be considered to be limited to any particular number of instruments unless expressly called for in the claims.

As shown in FIG. 1, each of the illustrated instruments 12A, 12B, 12C, 12D, 12E, 12F of the set 10 has a proximal end 11A, 11B, 11C, 11D, 11E, 11F and an opposite distal end. As used herein, "proximal" refers to the end or portion nearer to the surgeon, and "distal" refers to the end or portion further from the surgeon.

It should be understood that the illustrated instrument set is designed for use in sizing meniscal implants; variations may be made in the illustrated instrument set for application to use at other tissue sites in the patient's body.

As shown in FIG. 1, each illustrated instrument 12A, 12B, 12C, 12D, 12E, 12F in the set 10 includes an elongated hollow tube 14A, 14B, 14C, 14D, 14E, 14F and an elongated sizing template 16A, 16B, 16C, 16D, 16E, 16F. Each tube 14A, 14B, 14C, 14D, 14E, 14F has a distal end 18A, 18B, 18C, 18D, 18E, 18F and a proximal end (shown at 32D and 32A in FIGS. 5 and 8). Each sizing template 16A, 16B, 16C, 16D, 16E, 16F has a proximal end 19A, 19B, 19C, 19D, 19E, 19F, a straight intermediate portion 20A, 20B, 20C, 20D, 20E, 20F and a distal end 21A, 21B, 21C, 21D, 21E, 21F. As shown in FIG. 1, each illustrated instrument includes a handle assembly 26A, 26B, 26C, 26D, 26E, 26F. The handle assemblies receive the proximal ends of the hollow tubes 14A, 14B, 14C, 14D, 14E, 14F, as described in more detail below.

The illustrated instrument set 10 includes instruments with three different styles of elongate tubes. Three of the illustrated instruments 12A, 12B, 12C have tubes 14A, 14B, 14C that are straight along their entire length from the proximal to distal end. Three of the illustrated instruments 12D, 12E, 12F have tubes 14D, 14E, 14F that are straight for the majority of their lengths but that are curved near the distal ends 18D, 18E, 18F. In three of the instruments 12D, 12E, 12F the curved portions of the tubes curve to the side; the instruments can curve to the left or to the right (in a top plan view) by adjusting the tube 14D, 14E, 14F. With these different tube configurations available in the instrument set, the surgeon can select the most appropriate instrument for the particular defect site and surgical approach. It should be understood that the illustrated variations in tube shapes are provided as examples only; the present invention is not limited to any particular shape of tube or to any particular number of choices available to the surgeon unless expressly called for in the claims.

Figure 2:
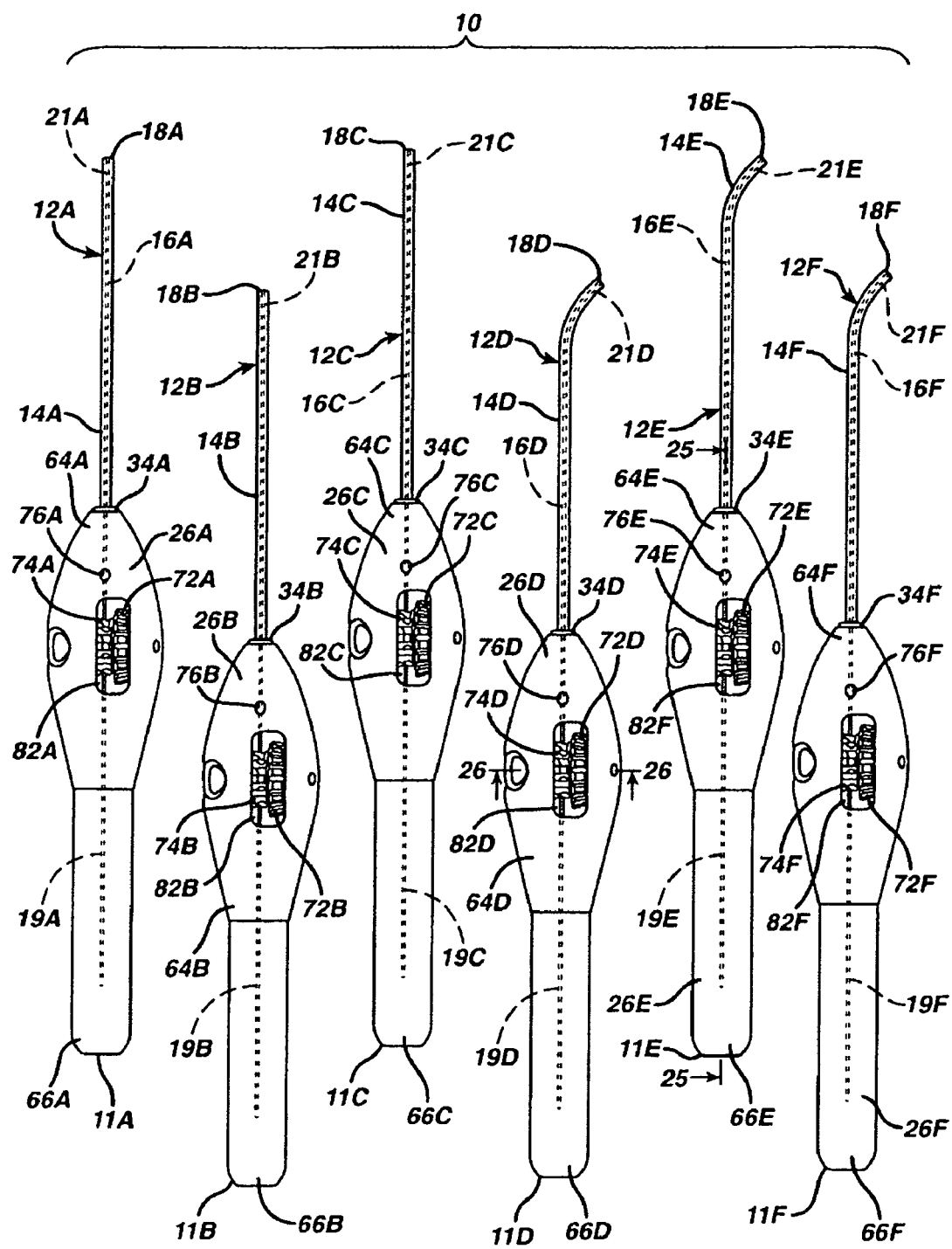
FIG. 2 is a top plan view of the surgical instruments of FIG. 1 with sizing templates in a retracted position.
Figure 3:
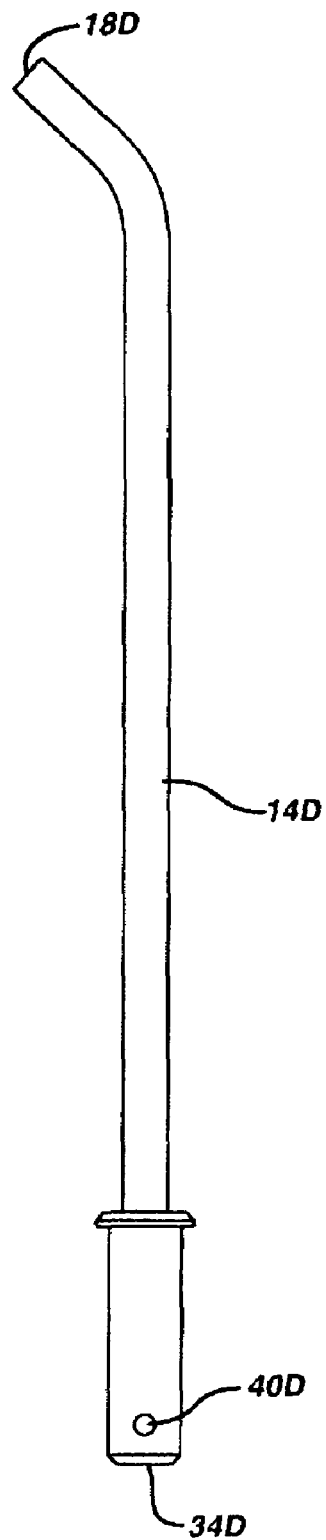
FIG. 3 is a bottom plan view of the tube and shoulder assembly of some of the instruments of FIGS. 1-2.
Figure 4:
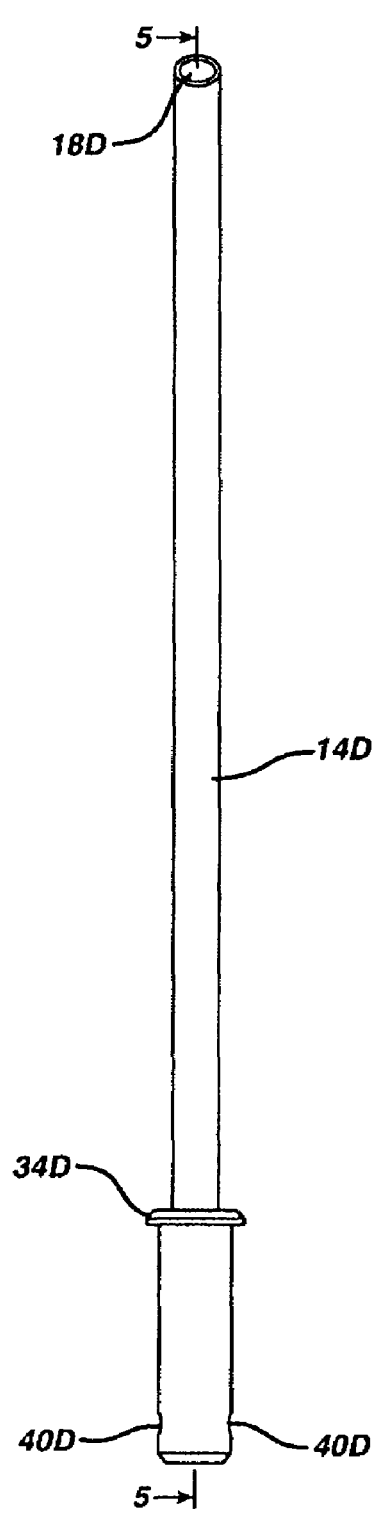
FIG. 4 is a side elevation of the tube and shoulder assembly of FIG. 3.

FIGS. 3-8 illustrate two of the hollow tubes 14A, 14D of the instruments of FIGS. 1-2. For simplicity, only these illustrated tubes 14A, 14D are described below. However, it should be understood that the following description applies to all of the hollow tubes 14A, 14B, 14C, 14D, 14E, 14F unless an express distinction is made for a particular type of tube.

Figure 5:
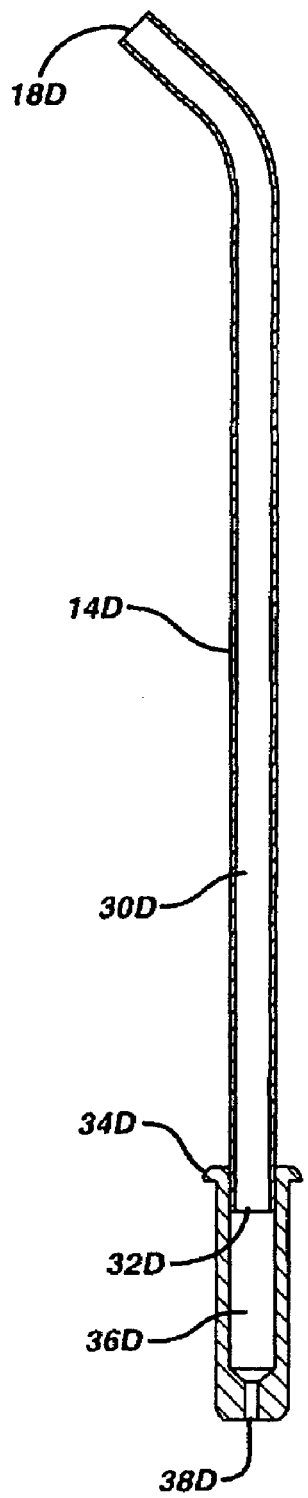
FIG. 5 is a cross-section of the tube and shoulder assembly of FIGS. 3-4, taken along line 5-5 of FIG. 4.
Figure 6:
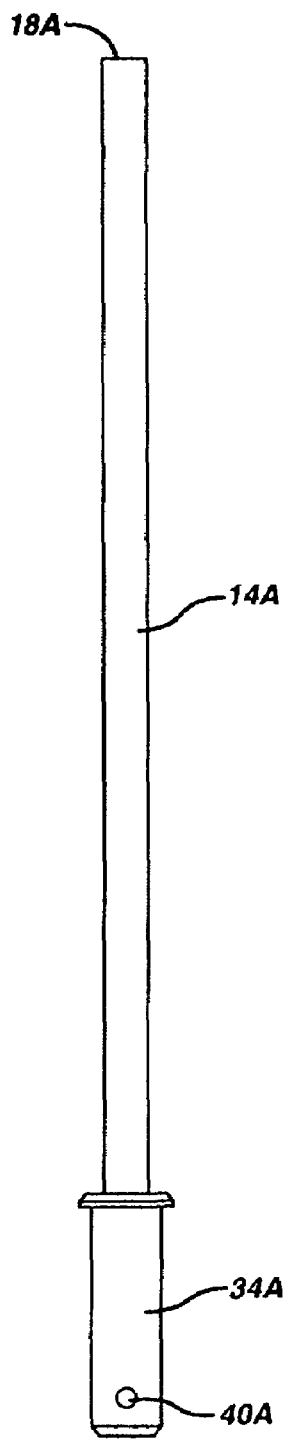
FIG. 6 is a bottom plan view of the tube and shoulder assembly of other instruments in the set of FIGS. 1-2.
Figure 7:
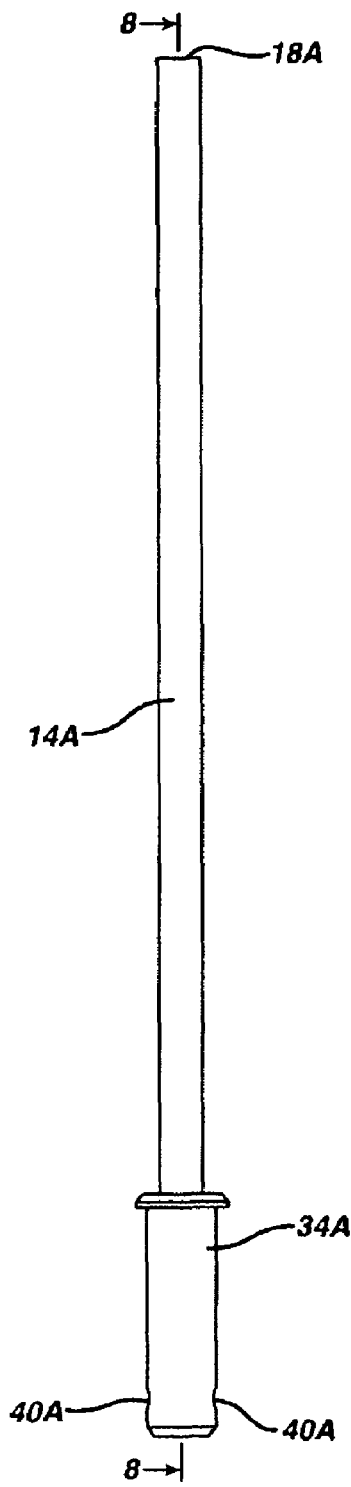
FIG. 7 is a side elevation of the tube and shoulder assembly of FIG. 6.
Figure 8:
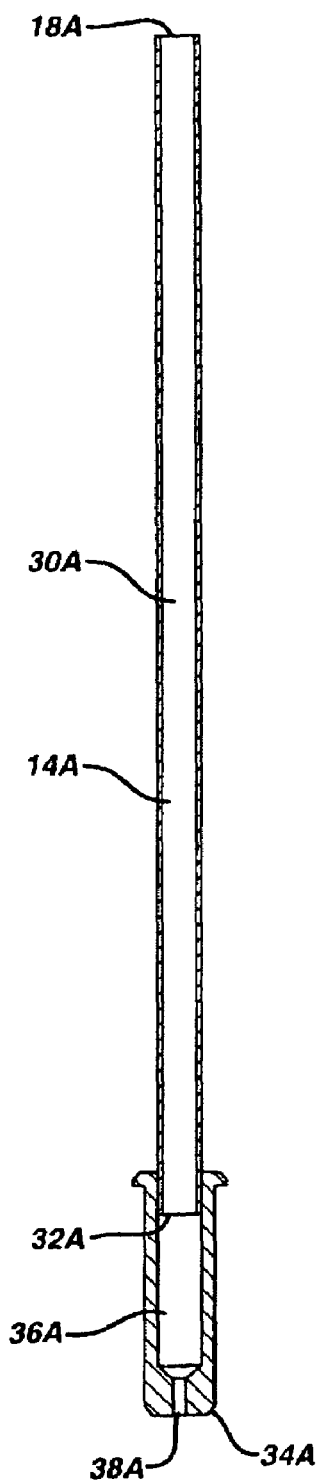
FIG. 8 is a cross-section of the tube and shoulder assembly of FIGS. 6-7, taken along line 8-8 of FIG. 7.

As shown in FIGS. 5 and 8, the hollow tubes 14A, 14D define longitudinal channels 30A, 30D. The channels 30A, 30D are open at the proximal end 32A, 32D and distal end 18A, 18D of the tubes 14A, 14D. The proximal ends 32A, 32D of the tubes 14A, 14D are received in shoulder components 34A, 34D. As shown in FIGS. 5 and 8, the shoulder components 34A, 34D have a distal channel 36A, 36D and a reduced diameter proximal channel 38A, 38D. All of the channels 30A, 30D, 36A, 36D, 38A, 38D are co-axial.

The hollow tubes 14A, 14D may be made of any suitable medical grade material for instruments, such as 304 stainless steel tubing. In the illustrated embodiments, the straight hollow tube 14A is 4.25 inches long, has an outer diameter of 0.148 inches and an inner diameter of 0.118 inches. In the curved hollow tube 14D, the curved distal portion defines a 45° angle with the straight portion of the tube; the proximal straight portion has a length of about 3.525 inches and the tube has an overall length of 4.160 inches. The shoulders 34A, 34D may be made of any suitable medical grade material for instruments, such as 17-4 PH TYP 630 stainless steel, for example. The shoulders 34A, 34D and tubes 14A, 14D may be welded together or connected in any other manner to create the sub-assemblies illustrated in FIGS. 3-8. The proximal portions of the shoulder components 34A, 34D have diametrically-opposed dimples 40A, 40D for mounting the tube sub-assemblies to the handle assembly 26A, 26D, as described in more detail below.

The sizing templates 16A, 16B, 16C, 16D, 16E, 16F are reciprocable within the tubes 14A, 14B, 14C, 14D, 14E, 14F, within the shoulder components 34A, 34B, 34C, 34D, 34E, 34F and within the handle assemblies 26A, 26B, 26C, 26D, 26E, 26F in a proximal-distal direction and can be moved between extended positions and retracted positions. In FIG. 1, the instruments 12A, 12B, 12C, 12D, 12E, 12F of the set 10 are illustrated with the sizing templates 16A, 16B, 16C, 16D, 16E, 16F in their extended positions, wherein parts of the sizing templates are exposed beyond the distal ends 18A, 18B, 18C, 18D, 18E, 18F of the tubes 14A, 14B, 14C, 14D, 14E, 14F. The instrument set 10 of FIG. 1 is shown in FIG. 2 with the sizing templates 16A, 16B, 16C, 16D, 16E, 16F in the retracted position. In the retracted position, the distal end 21A, 21B, 21C, 21D, 21E, 21F of each sizing template is retracted into the corresponding tube of that instrument. When the sizing templates 16A, 16B, 16C, 16D, 16E, 16F are fully retracted, the distal ends of the instruments are at the distal ends 18A, 18B, 18C, 18D, 18E, 18F of the tubes; when the sizing templates 16A, 16B, 16C, 16D, 16E, 16F are fully extended, the distal ends of the instruments are at the distal ends 21A, 21B, 21C, 21D, 21E, 21F of the sizing templates.

In the illustrated instrument set 10, three different sizes of sizing templates are provided for each tube style. Generally, at least one instrument is included in the kit to correspond with each size of implant in the system. For example, if the implant system includes three sizes of meniscal implants, small, medium and large, the instrument set would include at least three sizing templates, small, medium and large.

Figure 9:
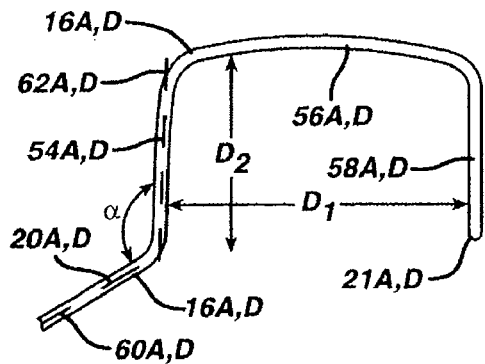
FIG. 9 is an enlarged top plan view of the distal end portion of the large sizing template of the instrument set of FIGS. 1-2.
Figure 10:
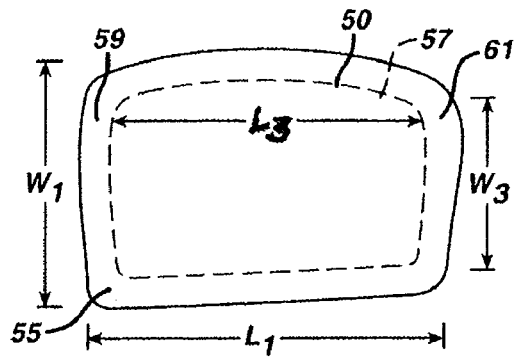
FIG. 10 is an enlarged top plan view of a large size meniscal implant that may be included as part of the system of the present invention.
Figure 11:
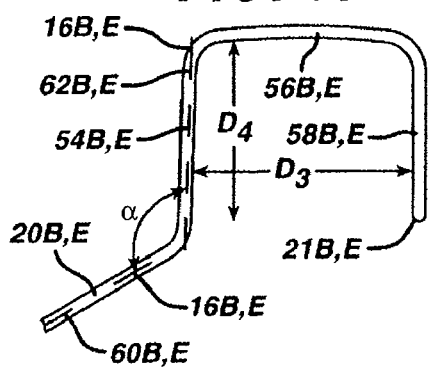
FIG. 11 is an enlarged top plan view of the distal end portion of the medium sizing template of the instrument set of FIGS. 1-2.
Figure 12:
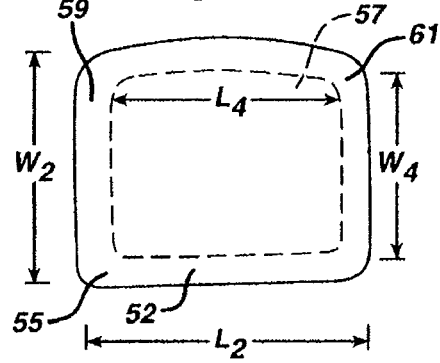
FIG. 12 is an enlarged top plan view of a medium size meniscal implant that may be included as part of the system of the present invention.
Figure 13:
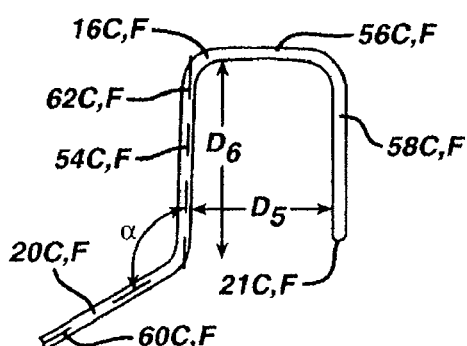
FIG. 13 is an enlarged top plan view of the distal end portion of the small sizing template of the instrument set of FIGS. 1-2.
Figure 14:
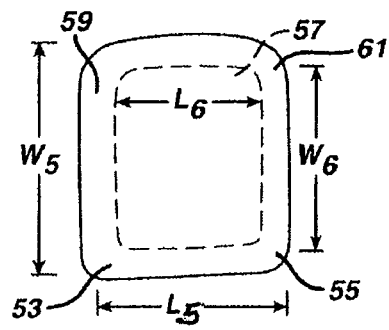
FIG. 14 is an enlarged top plan view of a small size meniscal implant that may be included as part of the system of the present invention.
Figure 15:
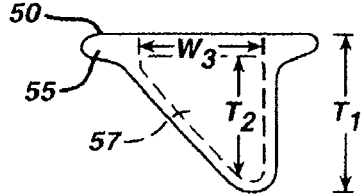
FIG. 15 is an end view of one of the meniscal implants of FIGS. 10, 12 and 14.

Three sizes of meniscal implants are illustrated in FIGS. 10, 12 and 14. FIG. 10 illustrates a large size meniscal implant 50 and FIG. 9 illustrates an example of the distal end 21A, 21D of a sizing template 16A, 16D that corresponds with this large sized implant 50. FIG. 12 illustrates a medium size meniscal implant 52 and FIG. 11 illustrates an example of the distal end 21B, 21E of a sizing template 16B, 16E that corresponds with this medium size implant 52. FIG. 14 illustrates a small size meniscal implant 53 and FIG. 13 illustrates an example of the distal end 21C, 21F of a sizing template 16C, 16F that corresponds with this small size implant 53. All three implants 50, 52, 53 have a similar shape in end view; a representative end view of the large implant 50 is illustrated in FIG. 15, showing the wedge-shape of the implant.

Each of the three illustrated meniscal implants 50, 52, 53 includes a cover 55 and a wedge 57. As illustrated, the top portion of the cover 55 extends over and beyond the sides or edges of the wedge 55 to provide fixation areas 59, 61. The fixation areas 59, 61 may be used to suture or otherwise fix the implant 50, 52, 53 to native tissue or bone, and the wedge 55 generally fills the gap in the native meniscal tissue left after a partial meniscetomy. It is anticipated that surgeons will trim the fixation areas 59, 61 intra-operatively to suit the needs of the individual patient. The cover 55 may comprise a laminate of sheets of tissue repair material, and the wedge 57 may also comprise tissue repair material, as disclosed in U.S. patent application Ser. No. 10/747,349, entitled "Implantable Tissue Repair Device and Method," filed on Dec. 29, 2003 by Malaviya et al., which is incorporated by reference herein in its entirety. The therapeutic implant, method of making the implant, and method of repairing cartilage using the implant may include the teachings of the following United States patent applications, the complete disclosures of which are incorporated by reference herein: Ser. No. 10/172,347 entitled "Hybrid Biologic-Synthetic Bioabsorbable Scaffolds" (U.S. Patent Publication No. 20030023316A1); Ser. No. 10/195,334 entitled "Cartilage Repair and Regeneration Scaffolds and Method" (U.S. Patent Publication No. 20030033021A1); Ser. No. 10/195,341 entitled "Hybrid Biologic/Synthetic Porous Extracellular Matrix Scaffolds" (U.S. Patent Publication No. 20030021827A1); Ser. No. 10/195,344 entitled "Unitary Surgical Device and Method" (U.S. Patent Publication No. 20030078617A1); Ser. No. 10/195,354 entitled "Porous Extracellular Matrix Scaffold and Method" (U.S. Patent Publication No. 20030044444A1); Ser. No. 10/195,606 entitled "Cartilage Repair and Regeneration Device and Method" (U.S. Patent Publication No. 20030033022A1); Ser. No. 10/195,633 entitled "Porous Delivery Scaffold and Method" (U.S. Patent Publication No. 2003-0049299A1); Ser. No. 10/195,719 entitled "Devices from Naturally Occurring Biologically Derived Materials" (U.S. Patent Publication No. 20030032961A1); and Ser. No. 10/195,794 entitled "Meniscus Regeneration Device and Method" (U.S. Patent Publication No. 20030036797A1). It should be understood that the particular implants, features of the implants, methods of making the implants and methods of repairing cartilage are provided as examples only; the present invention is not limited to the illustrated implants or to meniscal implants or to any particular method of making or using implants unless expressly called for in the claims.

As shown in FIGS. 10, 12 and 14-15, each of the illustrated implants 50, 52, 53 has an overall length $L_1, L_2, L_5$ between the side edges of the cover 55, an overall width $W_1, W_2, W_5$ between the front and back edges of the cover 55, and a maximum thickness $T_1$ between the top and bottom surfaces of the cover 55. The wedge portion 57 of each implant 50, 52, 53 has a length $L_3, L_4, L_6$ between the side edges of the wedge 57, a width $W_3, W_4, W_6$ between the front and back edges of the wedge 57, and a maximum thickness $T_2$ between the top and bottom surfaces of the wedge 57. In the illustrated embodiments: $L_1$ is about 1.30 inches; $L_2$ is about 1.11 inches; $L_5$ is about 0.91 inches; $L_3$ is about 0.98 inches; $L_4$ is about 0.79 inches; $L_6$ is about 0.59 inches; $W_1$ is about 0.87 inches; $W_2$ is about 0.87 inches; $W_5$ is about 0.87 inches; $W_3$, $W_4$, $W_6$ are about 0.47 inches; $T_1$ is about 0.31 inches; and $T_2$ is about 0.22 inches. It should be understood that these dimensions are provided as examples only; the present invention is not limited to any particular dimension unless expressly called for in the claims.

As shown in FIGS. 9,11 and 13, the sizing templates 16A, 16B, 16C, 16D, 16E, 16F corresponding with each implant size have first sides or segments 54A, 54B, 54C, 54D, 54E, 54F adjacent to the intermediate portions 20A, 20B, 20C, 20D, 20E, 20F of the sizing templates. The sizing templates have second sides or segments 56A, 56B, 56C, 56D, 56E, 56F adjacent to the first sides or segments 54A, 54B, 54C, 54D, 54E, 54F. Third sides or segments 58A, 58B, 58C, 58D, 58E, 58F are at the distal ends 21A, 21B, 21C, 21D, 21E, 21F of the sizing templates. In each sizing template, the second side or segment 56A, 56B, 56C, 56D, 56E, 56F is between the first side or segment 54A, 54B, 54C, 54D, 54E, 54F and third side or segment 58A, 58B, 58C, 58D, 58E, 58F.

Although each of the illustrated sizing templates 16A-16F has three sides or segments 54A-54F, 56A-56F and 58A-58F, it should be understood that fewer or additional segments in different shapes could be used. The invention is not limited to any particular number or shape of the distal end of the sizing template unless expressly called for in the claims.

In addition, in the instrument set 10 of FIGS. 1 and 2, the three sides or segments 54A-54F, 56A-56F, 58A-58F are all resilient. However, as described below with respect to FIGS. 29 and 30, the sides or segments comprising the template need not be resilient, and the present invention is not limited to resilient templates unless expressly called for in the claims.

As illustrated in FIGS. 9, 11 and 13, the intermediate portion 20A, 20B, 20C, 20D, 20E, 20F of each sizing template 16A, 16B, 16C, 16D, 16E, 16F has a central longitudinal axis 60A, 60B, 60C, 60D, 60E, 60F. The first segment 54A, 54B, 54C, 54D, 54E, 54F of each sizing template has a longitudinal axis 62A, 62B, 62C, 62D, 62E, 62F defining an angle $\alpha$ with the central longitudinal axis 60A, 60B, 60C, 60D, 60E, 60F of the intermediate portion 20A, 20B, 20C, 20D, 20E, 20F. In the illustrated embodiments, the angle $\alpha$ is 120° when the sizing template 16A, 16B, 16C, 16D, 16E, 16F is in its extended position, although it should be understood that the invention is not limited to any particular angle unless expressly set forth in the claims. The second segment 56A, 56B, 56C, 56D, 56E, 56F in each of the illustrated embodiments is curved, having a radius of 1.47 inches, although it should be understood that the invention is not limited to any particular radius or to a curved shape unless expressly set forth in the claims. The third segment 58A, 58B, 58C, 58D, 58E, 58F in each illustrated sizing template is substantially parallel to the first segment 54A, 54B, 54C, 54D, 54E, 54F when in the extended position, and has a blunt distal end. Each of the illustrated sizing templates 16A, 16B, 16C, 16D, 16E, 16F comprises an elongated wire having an outer diameter of 0.03 inches along its entire length, although it should be understood that the invention is not limited to any particular diameter of sizing template unless expressly set forth in the claims. For each of the three illustrated sizing templates, the three distal segments 54A-54F, 56A-56F, 58A-58F define an overall U-shape in plan view, although the invention is not limited to such a shape unless expressly called for in the claims.

Each of the illustrated large sizing templates 16A, 16D has a dimension $D_1$ between the first segment 54A, 54D and the third segment 58A, 58D of 0.98 inches and a dimension $D_2$ corresponding with the lengths of the first segment 54A, 54D and third segment 58A, 58D of 0.47 inches. Each of the illustrated medium sizing templates 16B, 16E has a dimension $D_3$ between the first segments 54B, 54E and the third segment 58B, 58E of 0.79 inches and a dimension $D_4$ corresponding with the lengths of the first segment 54B, 54E and third segment 58B, 58E of 0.47 inches. Each of the illustrated small sizing templates 16C, 16F have a dimension $D_5$ between the first segment 54C, 54F and the third segment 58C, 58F of 0.59 inches and a dimension $D_6$ corresponding with the lengths of the first segment 54C, 54F and third segment 58C, 58F of 0.47 inches. It should be understood that all of these dimensions are provided as examples only; the present invention is not limited to any particular dimension unless expressly called for in the claims.

In each of the illustrated embodiments, the three segments 54A-54F, 56A-56F, 58A-58F of each sizing template 16A-16F are co-planar with the respective intermediate portion 20A-20F. However, it should be understood that the segments could be angled to lie in a separate plane. In addition, the one or more of the segments could lie in a plane separate from that of the other segments.

Thus, for the large sizing template 16A, 16D, the distance $D_1$ corresponds with the length $L_3$ of the wedge 57 of the large size implant 50 and the distance $D_2$ corresponds with the width $W_3$ of the wedge 57 of the large size implant 50. For the medium sizing template 16B, 16E, the distance $D_3$ corresponds with the length $L_4$ of the wedge 57 of the medium size implant 52 and the distance $D_4$ corresponds with the width $W_4$ of the wedge 57 of the medium size implant 52. For the small sizing template 16C, 16F, the distance $D_5$ corresponds with the length $L_6$ of the wedge 57 of the small size implant 53 and the distance $D_6$ corresponds with the width $W_6$ of the wedge 57 of the small size implant 53. It should be understood that these correspondences in dimensions between the wedges of the implants and the sizing templates are provided as examples only; the sizing templates could instead be set to correspond for example with the outer dimensions of the covers 55 of the implants, or with some other feature of the implant as well. Accordingly, the present invention should not be limited to any particular correspondence of template size and implant size unless expressly set forth in the claims.

For each of the illustrated sizing templates, all three segments 54A-54F, 56A-56F, and 58A-58F are exposed outside of the distal ends 18A-18F of the respective tubes 14A-14F when the sizing template 16A-16F is in the extended position. All three segments 54A-54F, 56A-56F and 58A-58F are held within the channels 30A-30F of the respective tubes 14A-14F when the sizing template 16A-16F is in the retracted position.

Figure 19:
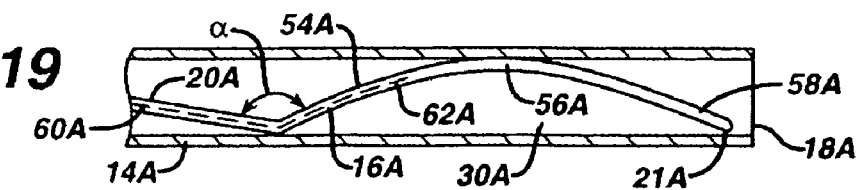
FIG. 19 is a cross-section of the distal end of the straight tube of one of the instruments of FIGS. 1-2, shown with the large sizing template in a retracted position.
Figure 20:
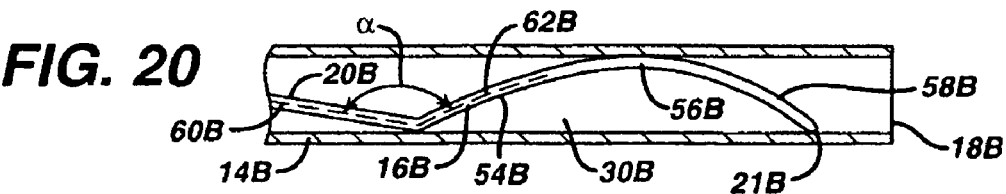
FIG. 20 is a cross-section of the distal end of the straight tube of another of the instruments of FIGS. 1-2, shown with the medium sizing template in a retracted position.
Figure 21:
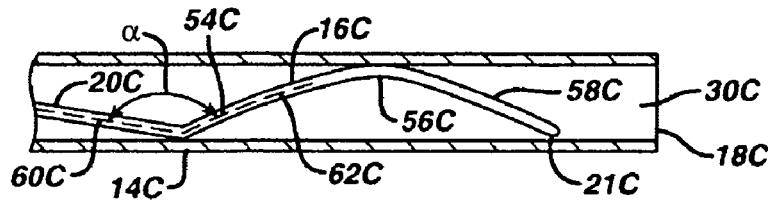
FIG. 21 is a cross-section of the distal end of the straight tube of another of the instruments of FIGS. 1-2, shown with the small sizing template in a retracted position.
Figure 22:
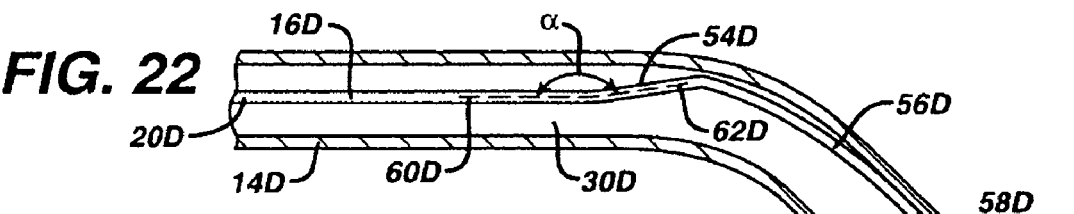
FIG. 22 is a cross-section of the distal end of the angled tube of one of the another of the instruments, shown with the large sizing template in a retracted position.
Figure 23:
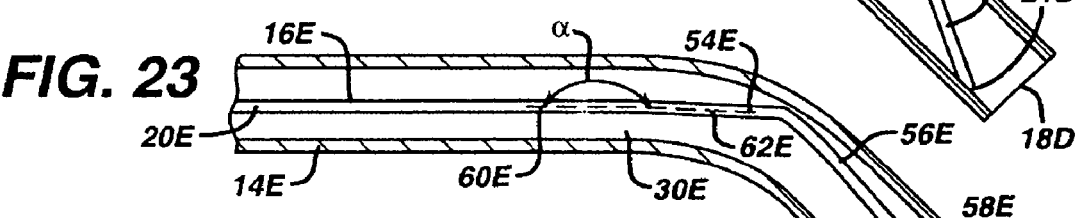
FIG. 23 is a cross-section of the distal end of the angled tube of one of the another of the instruments, shown with the medium sizing template in a retracted position.
Figure 24:
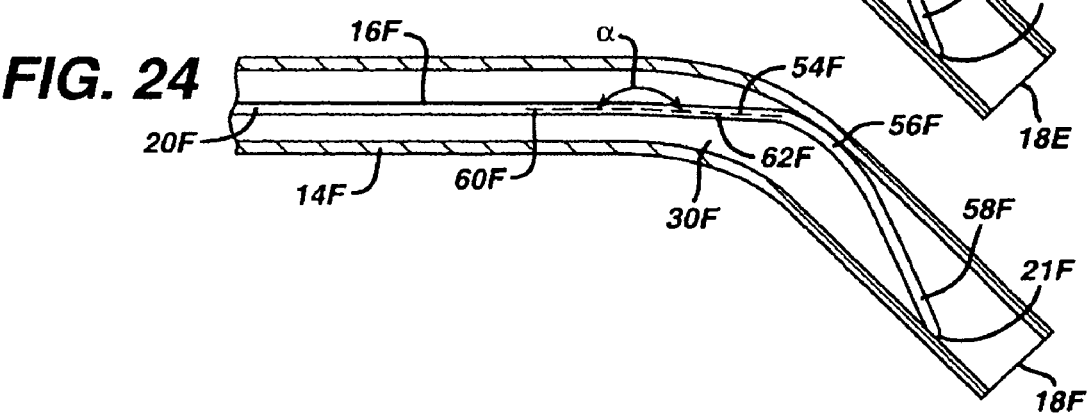
FIG. 24 a cross-section of the distal end of the angled tube of one of the another of the instruments, shown with the small sizing template in a retracted position.

FIG. 19 illustrates the large sizing template 16A in the retracted position within the straight tube 14A; FIG. 20 illustrates the medium sizing template 16B in the retracted position within the straight tube 14B; and FIG. 21 illustrates the small sizing template 16C in the retracted position within the straight tube 14C. FIG. 22 illustrates the large sizing template 16D in the retracted position within the angled tube 14D; FIG. 23 illustrates the medium sizing template 16E in the retracted position within the angled tube 14E; and FIG. 24 illustrates the small sizing template 16F in the retracted position within the angled tube 14F.

To allow the sizing templates 16A, 16B, 16C, 16D, 16E, 16F to be repeatedly retracted and extended, and to regain the desired shape in the extended position, the sizing templates may be made of a super-elastic or shape-memory material. The template material should be one that can be shaped into a pre-determined shape (such as the shapes illustrated in FIGS. 9, 11, 13 and 16-18), have sufficient rigidity to retain its pre-determined shape when extended over a distance such as 10-50 mm, that can deform to fit within the shape of the channel 30A-30F of the tube 14A-14F when retracted, and that will regain its pre-determined shape when extended beyond the channel. Finally, the material should be one that is suitable for surgical use. An example of a suitable material is nitinol (nickel-titanium alloy). It is anticipated that other alloys and other materials such as polymers and composites will also be usable as a shape memory material for the rulers. Accordingly, the present invention should not be limited to any particular material unless expressly called for in the claims.

To ease movement of the sizing templates 16A, 16B, 16C, 16D, 16E, 16F extended and retracted positions, the handle assembly 26A-26F of the illustrated instrument set 10 utilizes a gear mechanism that the surgeon can manipulate with the thumb or finger of the same hand that is used to grasp the handle assembly 26A-26F. The handle assembly 26A-26F in each of the illustrated instruments is the same.

Figure 25:
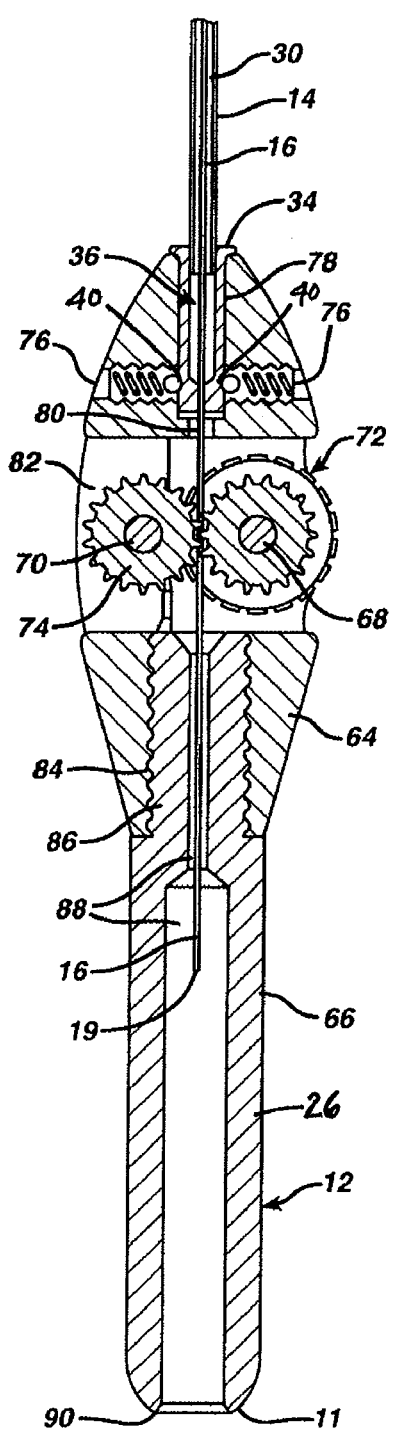
FIG. 25 is a longitudinal cross-section of the handle assembly of one of the instruments of FIGS. 1-2, taken along line 25-25 of FIG. 2.
Figure 26:
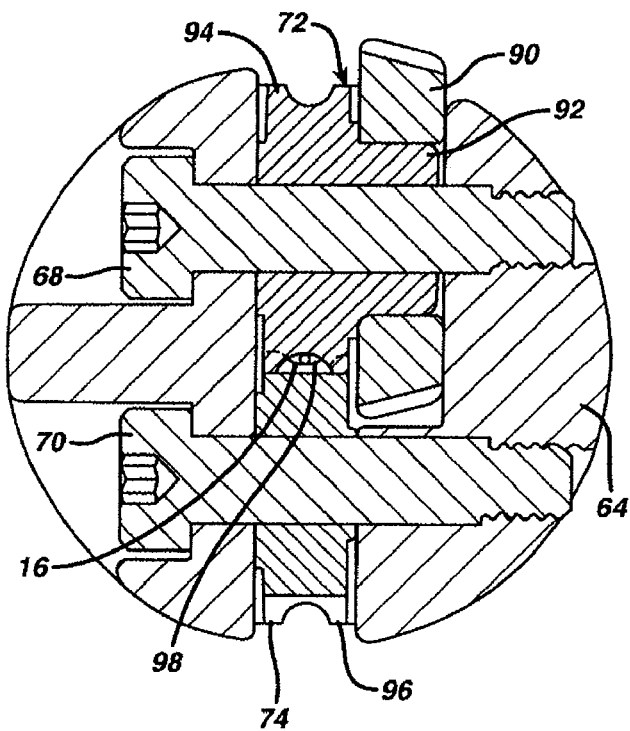
FIG. 26 is a transverse cross-section of the handle assembly of one of the instruments of FIGS. 1-2, taken along line 26-26 of FIG. 2.

A representative handle assembly is shown in longitudinal cross-section in FIG. 25 and in transverse cross-section in FIG. 26. In FIGS. 25 and 26 and in the following description of the handle assemblies, reference numbers are used without letter designations to indicate that the illustration and description applies to the handle assemblies 26A, 26B, 26C, 26D, 26E, 26F of all the illustrated instruments 12A, 12B, 12C, 12D, 12E, 12F.

As shown in FIG. 1, the handle assembly 26 includes a base 64A-64F, a handle post 66A-66F, a thumb gear assembly 72A-72F, a spur gear 74A-74F and two ball plungers 76A-76F. As shown in FIG. 24, the handle assembly also includes two screws 68, 70. A cross-section of a representative handle assembly 26 is shown in FIG. 25. As there shown, the base 64 has a distal longitudinal channel 78 and two transverse bores in communication with the distal longitudinal channel. The distal longitudinal channel 78 receives the shoulder 34 of the tube assembly, and the two ball plungers 76 are inserted into the bores to engage the dimples 40 in the shoulder 34 to thereby mount the tube assembly to the handle assembly 26. The distal longitudinal channel 78 communicates with a longitudinal distal bore 80, which communicates with a central open area 82, which communicates with a longitudinal female threaded opening 84. The female threaded opening 84 receives a distal male threaded portion 86 of the post 66. The post 66 includes a longitudinal channel 88 that communicates with the central open area 82 and extends to or near the proximal end 90 of the post 66. The distal longitudinal channel 78 and longitudinal distal bore 80 of the base 64 and longitudinal channel 88 of the post 66 are co-axial with the channel 30 of the tube 14. The sizing template 16 extends through the tube 14, through the distal channel 36 of the shoulder 34, through the reduced diameter proximal channel 38 of the shoulder 34, through the longitudinal distal bore 80 of the base 64, through the central open area 82 of the base and through the longitudinal channel 88 of the post 66. In the central open area 82 of the base 64, the sizing template 16 passes between the thumb gear assembly 72 and the spur gear 74.

In the illustrative handle of FIGS. 25 and 26, the thumb gear assembly 72 is mounted to the base 64 by the screw 68 and the spur gear 74 is mounted to the base 64 by the screw 70. The thumb gear assembly 72 is freely rotatable on the smooth shaft of the screw 68 and the spur gear 74 is freely rotatable on the smooth shaft of the screw 70.

In the illustrative handle of FIGS. 25-26, the thumb screw assembly 72 comprises a thumb wheel 90 and a thumb gear 92 mounted coaxially on the screw 68. The outer surface of the thumb wheel 90 has a plurality of axial splines 94 so that the surgeon can easily rotate the wheel 90 with a thumb or finger. The thumb wheel 90 receives a reduced diameter portion of the thumb gear 92 so that the thumb wheel 90 and thumb gear 92 rotate together.

Figure 27:
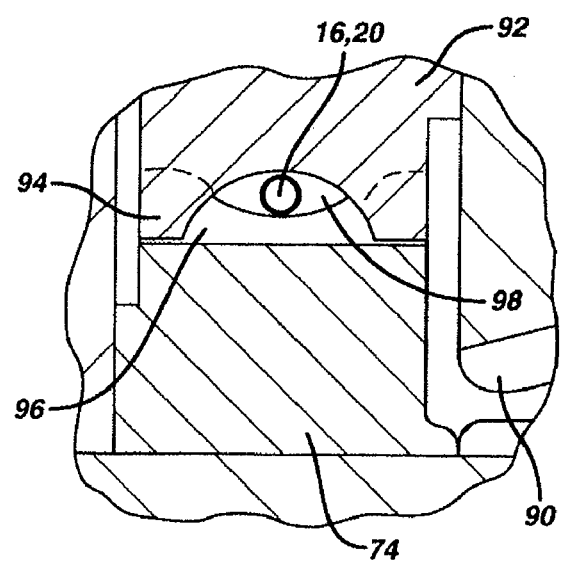
FIG. 27 is an enlarged view of a portion of FIG. 26, showing a sizing template in a passageway defined by grooves in the intermeshing teeth of two gears.

In the illustrative handle of FIGS. 26-27, the thumb gear 92 has a plurality of grooved teeth 94 that intermesh with the grooved teeth 96 of the spur gear 74. As shown in FIG. 26, the intermeshing grooved teeth 94 of the thumb gear 92 and grooved teeth 96 of the spur gear 74 define a passageway 98 that is co-axially aligned with the distal longitudinal channel 78 and longitudinal distal bore 80 of the base 64 and longitudinal channel 88 of the post 66. The intermediate portion 20 of the sizing template 16 extends between the thumb gear 92 and the spur gear 74, passing through the passageway 98 defined by the grooved teeth 94, 96. Where the proximal surface of one of the thumb gear teeth 94 meets and engages the distal surface of one of the spur gear teeth 96, at least one of the transverse dimensions of the passageway 98 is slightly less than the outer diameter of the intermediate portion 20 of the sizing template 16 so that the mating teeth 94, 96 grip the sizing template 16. Thus, the sizing template 16 can be reciprocated in the proximal-distal direction by rotating the thumb wheel 90, and the surgeon can extend and retract the sizing template 16 with the same hand used to grasp the handle post 66.

All of the components of the handle assembly 26A-26F can be made of standard materials for surgical instruments. For example, the base 64A-64F and post 66A-66F can be made of acetyl co-polymer, and the gears 74A-74F, 92, thumb wheel 90, screws 68, 70 and ball plungers 76A-76D can be made of stainless steel. It should be understood that all of these materials are identified as examples only; the present invention is not limited to any particular material unless expressly called for in the claims.

Use of the illustrated instrument set 10 is described below and illustrated in FIG. 28 in treating a defect 100 in the meniscus 102. In the illustrations, the tissue defect 100 comprises a gap in the posterior portion of the medial horn 104 of the meniscus 102 created by a partial meniscectomy. Although not described in detail below, it should be understood that the technique described below may also be used in treating tissue defects in other areas of the medial horn 104 of the meniscus as well as in the lateral horn 106 of the meniscus. It should also be understood that the technique described below may also be applied in treating defects at other tissue sites in a patient's body. In FIG. 28, a portion of the anterior cruciate ligament is shown at 108 and a portion of the posterior cruciate ligament is shown at 110.

The surgeon can perform standard arthroscopic procedures to create portals to gain access to the medial horn 104 of the meniscus. Standard cannulae can be inserted through the portals, and a standard arthroscope (not shown) can be used for visualization of the tissue site. An appropriate sizing instrument, for example the medium instrument with a 45° offset is selected. It should be understood that the selection of the shape of the sizing instrument will depend on the defect site, surgical approach and surgeon preference. The 45° offset instrument is discussed below as an example only.

In the case illustrated in FIG. 28, because of the defect site and surgical approach, the 45° offset sizing instrument has been flipped 180° from the position illustrated in FIG. 1 so that the bottom side of the instrument is facing up and so that the distal end 18E of the tube 14E is angled to the left. The surgeon selects the size of the sizing instrument based upon an initial approximation of the size of implant to be used to repair the defect.

The surgeon may then retract the three segments 54E, 56E, 58E into the channel 30 of the tube so that the sizing template 16E is in the retracted position shown in FIGS. 2 and 23. The tube 14E may then be inserted through one of the cannulae and guided to the medial meniscus 104.

When the distal end 18E of the tube 14E is in position at the medial meniscus 104, the surgeon may extend the sizing template by turning the thumb wheel 90 with a finger on the same hand that is used to hold the post 66 of the instrument. When the sizing template 16E has been fully extended to the positions shown in FIGS. 1 and 11, the surgeon can then move the sizing template 16E until the shaped segments 54E, 56E, 58E overlie or fit within the edges of the tissue defect 100. As illustrated in FIG. 28, the defect 100 is visible (either be means of the arthroscope or by eye if the instruments are used in open surgery) even with the shaped end of the sizing template 16E in place over or within the defect. If the surgeon is satisfied that an implant corresponding with the size of the template will be appropriate for the defect, the surgeon can then turn the thumb wheel 90 to retract the sizing template 16E and remove the instrument 12E. An implant may then be delivered and fixed implant in place. If the surgeon is not satisfied that the implant corresponding with that sizing template is appropriate, the surgeon can retract the sizing template, remove the instrument 12E and then follow the same procedure with the larger sizing instrument 12D or smaller sizing instrument 12F until satisfied that the most appropriate size of implant will be used.

Using the instrument set 10 with retractable and extendable sizing templates, the surgeon can use templates having shapes and sizes that would not normally fit through an arthroscopic cannula, and that could be damaged or become misshapen if introduced without a cannula.

To deliver the implant arthroscopically, devices may be used like those disclosed in the following United States patent applications, which are incorporated by reference herein in their entireties: U.S. patent application Ser. No. 10/610,287 entitled "Slide and Kit for Delivering Implants" (filed Jun. 30, 2003) and U.S. Provisional Patent Application Ser. No. 60/483,804 entitled "Instrument for Delivery of Implant" (filed Jun. 30, 2003). However, the present invention is not limited to any particular implant, surgical technique or surgical instrument unless expressly set forth in the claims.

Although the technique of the present invention has been described above with respect to an arthroscopic procedure, it should be understood that the instruments and technique of the present invention can also be used with more invasive surgical procedures, such as a mini-arthrotomy or an open surgical procedure.

While the illustrated instrument set 10 all utilize retractable sizing templates 16, it should be understood that some of the advantages of the present invention can also be obtained through use of instruments having a non-retractable sizing template. Examples of such instruments are illustrated in FIGS. 29-30. While the instruments of FIGS. 29-30 may not be as easily introduced to the defect site, they do offer advantages. The instrument 110 of FIG. 29 allows the surgeon to view the relationship between the size of the defect and the size of the template 112 without the template covering the defect, and both the instruments 110, 114 of FIGS. 29 and 30 offer the opportunity to determine the appropriate size of implant that best suits the size of the defect. The template portion 112, 116 of the instruments of FIGS. 29-30 can be made or stainless steel, a polymer or a composite, and can be designed to be reusable or disposable after each use, while the handle could also be designed to be reusable or disposable. The template portions 112, 116 of the instruments illustrated in FIGS. 29-30 have sides 118, 120, 122, 124, 126, 128 that correspond in length and orientation with sides or edges of the soft tissue implants. It should be understood that instrument sets utilizing the designs of FIGS. 29 and 30 would include several instruments with different sizes of distal ends, and would include instruments corresponding with the different sizes of implants available.

It should be appreciated that some of the features of the retractable instrument set 10 can also be applied to other types of surgical instruments. For example, a thumb gear assembly and spur gear on an instrument handle to extend and retract another component of the instrument can be applied to other surgical instruments, particularly those in which the component to be extended and retracted comprises a shape-memory material such as nitinol. One example of such a possible use of the intermeshing gears is in the United States Provisional Patent Application filed concurrently herewith by Anthony D. Zannis, Jack Farr, M.D., Randall L. Holcomb, M.D., Herbert E. Schwartz, Prasanna Malaviya, Keith M. McGrath, Danny E. McAdams and Andrew M. Jacobs and entitled "Coordinate Instrument Set", the complete disclosure of which is incorporated by reference herein.

While only specific embodiments of the invention have been described and shown, it is apparent that various alternatives and modifications can be made thereto. Those skilled in the art will also recognize that certain additions can be made to the illustrative embodiments. It is, therefore, the intention in the appended claims to cover all such alternatives, modifications and additions as may fall within the true scope of the invention.

We claim:

1. A surgical sizing instrument set comprising:
 a first surgical sizing instrument including:
  a hollow tube having a proximal end and a distal end;
   an elongated sizing template extending through the hollow tube, the elongated sizing template having:
    a proximal end;
    a distal end;
    an intermediate portion between the proximal end and distal end;
    a first resilient segment adjacent to the intermediate portion;
    a second resilient segment adjacent to the first resilient segment and positioned between the first resilient segment and the distal end of the elongated sizing template;
   wherein the elongated sizing template is reciprocable in the hollow tube between an extended position and a retracted position; and
   wherein the first resilient segment and second resilient segment have a first angular relationship when the elongated sizing template is in the extended position and a second angular relationship when the elongated sizing template is in the retracted position, the first angular relationship being different from the second angular relationship;
 the surgical sizing instrument set further comprising a second surgical sizing instrument including:
  a hollow tube having a proximal end and a distal end;
   an elongated sizing template extending through the hollow tube, the elongated sizing template having:
    a proximal end;
    a distal end;
    an intermediate portion between the proximal end and distal end;
    a first resilient segment adjacent to the intermediate portion;
    a second resilient segment adjacent to the first resilient segment and positioned between the first resilient segment and the distal end of the elongated sizing template;

wherein the elongated sizing template is reciprocable in the hollow tube between an extended position and a retracted position; and wherein the first resilient segment and second resilient segment have a first angular relationship when the elongated sizing template is in the extended position and a second angular relationship when the elongated sizing template is in the retracted position, the first angular relationship being different from the second angular relationship;

wherein the length of at least one of resilient segments of the first surgical sizing instrument is greater than the length at least one of the resilient segments of the second surgical sizing instrument.

2. The surgical sizing instrument set of claim 1 wherein the elongated sizing template of each surgical sizing instrument comprises a shape-memory material.

3. The surgical sizing instrument set of claim 2 wherein the elongated sizing template of each surgical sizing instrument comprises nitinol.

4. The surgical sizing instrument set of claim 1 wherein the elongated sizing template of each surgical sizing instrument comprises a super-elastic material.

5. The surgical sizing instrument set of claim 4 wherein the super-elastic material comprises nitinol.

6. The surgical sizing instrument set of claim 1 wherein the hollow tube of the first surgical sizing instrument is straight along its entire length.

7. The surgical sizing instrument set of claim 1 wherein the hollow tube of the second surgical sizing instrument includes a straight portion and a distal portion defining an obtuse angle with the straight portion.

8. The surgical sizing instrument set of claim 1 wherein the first surgical sizing instrument further comprises a body at the proximal end of the hollow tube, a spur gear mounted to the body and a thumb gear mounted to the body, the spur gear including grooved teeth and the thumb gear including grooved teeth intermeshed with the grooved teeth of the spur gear, the grooves of the intermeshed teeth defining a passageway having a transverse dimension, wherein the intermediate portion of the elongated sizing template extends through the passageway.

9. The surgical sizing instrument set of claim 8 wherein the intermediate portion of the elongated sizing template has a transverse dimension greater than the transverse dimension of the passageway.

10. The surgical sizing instrument set of claim 8 wherein the second surgical sizing instrument further comprises a body at the proximal end of the hollow tube, a spur gear mounted to the body and a thumb gear mounted to the body, the spur gear including grooved teeth and the thumb gear including grooved teeth intermeshed with the grooved teeth of the spur gear, the grooves of the intermeshed teeth defining a passageway having a transverse dimension, wherein the intermediate portion of the elongated sizing template extends through the passageway.

11. The surgical sizing instrument set of claim 10 wherein the intermediate portion of the elongated sizing template has a transverse dimension greater than the transverse dimension of the passageway.

12. A surgical implant system comprising:
a first implant having a width and a length;
a second implant having a width and a length, wherein at least one of the width and length of the second implant being larger than the corresponding dimension of the first implant;
a first surgical sizing instrument including:

a hollow tube having a proximal end and a distal end;
an elongated sizing template extending through the hollow tube, the elongated sizing template having:
a proximal end;
a distal end;
an intermediate portion between the proximal end and distal end;
a first resilient segment adjacent to the intermediate portion;
a second resilient segment adjacent to the first resilient segment and positioned between the first resilient segment and the distal end of the elongated sizing template;
wherein the elongated sizing template is reciprocable in the hollow tube between an extended position and a retracted position;
wherein the first resilient segment has a length corresponding with the width of the first implant and the second resilient segment has a length corresponding with the length of the first implant;
wherein the first resilient segment and second resilient segment have a first angular relationship when the elongated sizing template is in the extended position and a second angular relationship when the elongated sizing template is in the retracted position, the first angular relationship being different from the second angular relationship;
the surgical sizing instrument set further comprising a second surgical sizing instrument including:
a hollow tube having a proximal end and a distal end;
an elongated sizing template extending through the hollow tube, the elongated sizing template having:
a proximal end;
a distal end;
an intermediate portion between the proximal end and distal end;
a first resilient segment adjacent to the intermediate portion;
a second resilient segment adjacent to the first resilient segment and positioned between the first resilient segment and the distal end of the elongated sizing template;
wherein the elongated sizing template is reciprocable in the hollow tube between an extended position and a retracted position;
wherein the first resilient segment has a length corresponding with the width of the second implant and the second resilient segment has a length corresponding with the length of the second implant; and
wherein the first resilient segment and second resilient segment have a first angular relationship when the elongated sizing template is in the extended position and a second angular relationship when the elongated sizing template is in the retracted position, the first angular relationship being different from the second angular relationship.

13. The implant system of claim 12 wherein the first implant and second implant are sized and shaped to replace a portion of a meniscus.

14. The implant system of claim 12 wherein:
the first implant has an edge along its width and an edge along its length;
the second implant has an edge along its width and an edge along its length;
the shape of the first resilient segment of the first surgical sizing instrument corresponds with the shape of the edge along the width of the first implant;

the shape of the second resilient segment of the first surgical sizing instrument corresponds with the shape of the edge along the length of the first implant;

the shape of the first resilient segment of the second surgical sizing instrument corresponds with the shape of the edge along the width of the second implant; and the shape of the second resilient segment of the second surgical sizing instrument corresponds with the shape of the edge along the length of the second implant.

15. The implant system of claim 12 wherein the elongated sizing template of each surgical sizing instrument comprises a shape-memory material.

16. The implant system of claim 15 wherein the elongated sizing template of each surgical sizing instrument comprises nitinol.

17. The implant system of claim 12 wherein the elongated sizing template of each surgical sizing instrument comprises a super-elastic material.

18. The implant system of claim 17 wherein the super-elastic material comprises nitinol.

19. The implant system of claim 12 wherein the hollow tube of the first surgical sizing instrument is straight along its entire length.

20. The implant system of claim 19 wherein the hollow tube of the second surgical sizing instrument includes a straight portion and a distal portion defining an obtuse angle with the straight portion.

21. The implant system of claim 12 wherein the first surgical sizing instrument further comprises a body at the proximal end of the hollow tube, a spur gear mounted to the body and a thumb gear mounted to the body, the spur gear including grooved teeth and the thumb gear including grooved teeth intermeshed with the grooved teeth of the spur gear, the grooves of the intermeshed teeth defining a passageway having a transverse dimension, wherein the intermediate portion of the elongated sizing template extends through the passageway.

22. The implant system of claim 21 wherein the intermediate portion of the elongated sizing template has a transverse dimension greater than the transverse dimension of the passageway.

23. The implant system of claim 21 wherein the second surgical sizing instrument further comprises a body at the proximal end of the hollow tube, a spur gear mounted to the body and a thumb gear mounted to the body, the spur gear including grooved teeth and the thumb gear including grooved teeth intermeshed with the grooved teeth of the spur gear, the grooves of the intermeshed teeth defining a passageway having a transverse dimension, wherein the intermediate portion of the elongated sizing template extends through the passageway.

24. The implant system of claim 23 wherein the intermediate portion of the elongated sizing template has a transverse dimension greater than the transverse dimension of the passageway.

25. The implant system of claim 12 wherein the distal end of the hollow tube of each instrument has a maximum cross-sectional outer dimension of 12 mm.

* * * * *